(12) United States Patent
Martínez Gil et al.

(10) Patent No.: US 9,192,610 B2
(45) Date of Patent: Nov. 24, 2015

(54) USE OF QUINAZOLINE DERIVATIVES FOR NEURODEGENERATIVE DISEASES

(75) Inventors: Ana Martínez Gil, Madrid (ES); Carmen Gil Ayuso-Gontan, Madrid (ES); Concepción Pérez Martín, Madrid (ES); Ana Pérez Castillo, Madrid (ES); José Morales García, Madrid (ES); Miriam Redondo Sancho, Madrid (ES); Marina Sanz San Cristóbal, Madrid (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 590 days.

(21) Appl. No.: 13/321,046

(22) PCT Filed: May 20, 2010

(86) PCT No.: PCT/ES2010/070338
§ 371 (c)(1),
(2), (4) Date: Feb. 7, 2012

(87) PCT Pub. No.: WO2010/133742
PCT Pub. Date: Nov. 25, 2010

(65) Prior Publication Data
US 2012/0129877 A1 May 24, 2012

(30) Foreign Application Priority Data
May 20, 2009 (ES) .................................. 200930189

(51) Int. Cl.
*A61K 31/517* (2006.01)
(52) U.S. Cl.
CPC .................................... *A61K 31/517* (2013.01)
(58) Field of Classification Search
CPC .................................................. A61K 31/517
USPC .................................................... 514/266.31
See application file for complete search history.

(56) References Cited

U.S. PATENT DOCUMENTS

2005/0038051 A1* 2/2005 Nunnari et al. ............ 514/266.2
2008/0260643 A1 10/2008 Bergmann et al.

FOREIGN PATENT DOCUMENTS

WO    WO 2008/113881    9/2008

OTHER PUBLICATIONS

Yang, "Attenuation of MPTP neurotoxicity by rolipram, a specific inhibitor of phosphodiesterase IV", Experimental Neurology 211, 2008, pp. 311-314.*

Abdel-Salam, "Drugs Used to Treat Parkinson's Disease, Present Status and Future Directions." *CNS & Neurological Disorders—Drug Targets*, vol. 7, 2008, pp. 321-342.
Castano et al., "Synthesis, Structural Analysis, and Biological Evaluation of Thioxoquinazoline Derivatives as Phosphodiesterase 7 Inhibitors." *ChemMedChem*, vol. 4, 2009, pp. 866-876.
Dauer et al., "Parkinson's Disease: Mechanisms and Models." *Neutron*, vol. 39, Sep. 11, 2003, pp. 889-909.
Gallagher et al., "Impact of Newer Pharmacological Treatments on Quality of Life in Patients with Parkinson's Disease." *CNS Drugs*, vol. 22, No. 7, 2008, pp. 563-586.
Griess, "Bemerkungen zu der Abhandlung der HH Weselsky und Benedikt Ueber einige Azovergindungen." *Chem. Ber.*, 1879, 12, pp. 426-428.
Kieburtz, "Therapeutic Strategies to Prevent Motor Complications in Parkinson's Disease." *J. Neurol*, vol. 255, Supp. 4, 2008, pp. 42-45.
Kröncke et al., "Nitric Oxide: Cytotoxicity versus Cytoprotection—How, Why, When, and Where?" *Biology and Chemistry*, vol. 1, No. 2, Apr 1997, pp. 107-120.
Lang et al., "Parkinson's Disease—First of Two Parts." *The New England Journal of Medicine*, vol. 339, No. 15, Oct. 8, 1998, pp. 1044-1053.
Lang et al., "Parkinson's Disease—Second of Two Parts." *The New England Journal of Medicine*, vol. 339, No. 16, Oct 15, 1998, pp. 1130-1143.
LeWitt, "Levodopa Therapeutics for Parkinson's Disease: New Developments." *Parkinsonism and Related Disorders*, vol. 15, Supp. 1, 2009, pp. S31-S34.
Luna-Medina et al., "Regulation of Inflammatory Response in Neural Cells in Vitro by Thiadiazolidinones Derivatives through Peroxisome Proliferator-activated Receptor γ Activation." *The Journal of Biological Chemistry*, vol. 280, No. 22, Jun. 3, 2005, pp. 21453-21462.
Mendez et al., "Use of 6-Hydroxydopamine to Create Lesions in Catecholamine Neurons in Rats." *J. Neurosurg.*, vol. 42, Feb. 1975, pp. 166-173.
Poewe, "Treatments for Parkinson's Disease—Past Achievements and Current Clinical Needs." *Neurology*, vol. 72, Supp. 2, Feb. 17, 2009, pp. S65-S73.
Savitt et al., "Diagnosis and Treatment of Parkinson Disease: Molecules to Medicine." *The Journal of Clinical Investigation*, vol. 116, No. 7, Jul. 2006, pp. 1744-1754.
International Search Report for Application No. PCT/ES2010/070338 mailed Oct. 18, 2010.

* cited by examiner

*Primary Examiner* — Sreeni Padmanabhan
*Assistant Examiner* — Sahar Javanmard
(74) *Attorney, Agent, or Firm* — Marchant & Gould P.C.

(57) ABSTRACT

The present invention relates to the use of a series of quinazoline-derived compounds to produce a medicament for the treatment and/or prevention of neurological and/or neurodegenerative diseases, such as Parkinson's disease or Alzheimer's disease. The present invention also relates to a method for the treatment and/prevention of neurological and/neurodegenerative diseases comprising the administration of a therapeutically effective amount of said compounds.

11 Claims, 6 Drawing Sheets

A)

B)

USE OF QUINAZOLINE DERIVATIVES FOR NEURODEGENERATIVE DISEASES

This application is a National Stage Application of PCT/ES2010/070338, filed 20 May 2010, which claims benefit of Ser. No. P200930189, filed 20 May 2009 in Spain and which applications are incorporated herein by reference. To the extent appropriate, a claim of priority is made to each of the above disclosed applications.

TECHNICAL FIELD

The invention is directed to the field of medical chemistry and more specifically to heterocyclic derivatives of quinazolines and their potential for treating neurodegenerative and/or neurological diseases, among others Parkinson's disease, and therefore relates to the pharmaceutical sector.

STATE OF THE ART

Neurodegenerative diseases are one of the main causes of death in the Western world. Parkinson's disease (PD) is the second most common neurodegenerative disease after Alzheimer's disease (Dauer, W.; Przedborski, S., Parkinson's disease: mechanisms and models. Neuron 2003, 39,889-909), affecting approximately 15% of people aged over 65. Currently only symptomatic therapies are available which, although effective in the first stages of the disease have considerable long-term secondary effects. Therefore it is necessary to find new effective and safe therapies for treating this pathology.

PD is characterized by progressive death of the dopaminergic neurons of the substantia nigra pars compact (SNpc) (Lang, A E.; Lozano, A M., Parkinson's disease. First of two parts. The New England Journal of Medicine 1998, 339, 1044-1053 and Lang, A E.; Lozano, A M., Parkinson's disease. Second of two parts. The New England Journal of Medicine 1998, 339,1130-1143) and by inclusion bodies (Lewy's bodies) containing a-synuclein. The main consequence of this neuronal loss is a marked reduction in the brain's availability of dopamine in the caudate nucleus and putamen, areas where the dopaminergic neurons of SNpc are projected. This provokes a considerable dysfunction in the regulation of the main brain structures involved in controlling movement, the basal ganglia. Classic Parkinson's symptoms include dyskinesias (tremors of the hands, arms, legs and face), rigidity of the trunk and extremities, bradykinesia (slowness of movement) and postural instability with balancing problems.

The finding that PD was characterized by a loss of dopamine led to the discovery of therapies aimed at correcting this deficiency. These are palliative therapies, aimed at treating the symptoms of the disease but none of them manages to halt its progression (Savitt, J M.; Dawson, V L.; Dawson, T M., Diagnosis and treatment of Parkinson disease: molecules to medicine. J Clin Invest 2006, 116,1744-1754). Currently, the dopamine precursor, levodopa, is the most effective treatment in PD (LeWitt, P. A., Levodopa therapeutics for Parkinson's disease: new developments. Parkinsonism Relat Disord. 2009, Suppl 1,S31-4). This treatment is sometimes combined with other drugs such as peripheral decarboxylase inhibitors (carbidopa) (Abdel-Salam, O. M., Drugs used to treat Parkinson's disease, present status and future directions. CNS Neurol Disord Drug Targets. 2008, 7, 321-442), cathecol-O-methyl-transferase (COMT) inhibitors, which prolong the half life of levodopa (Gallagher, D. A.; Schrag, A., Impact of newer pharmacological treatments on quality of life in patients with Parkinson's disease. CNS Drugs. 2008, 22, 563-586) and dopamine agonists that directly stimulate the postsynaptic dopamine receptors (Kieburtz, K., Therapeutic strategies to prevent motor complications in Parkinson's disease. J Neurol. 2008, 255, Suppl 4, 42-45). Despite all these advances in the treatment of PD symptoms, their efficacy declines over time fundamentally due to the development of motor complications such as dyskinesias and dystonias.

In view of the major limitations presented by current therapies, both pharmacological and surgical, there is a need to develop other alternatives to slow down or stop the progress of the disease (Poewe, W., Treatments for Parkinson disease—past achievements and current clinical needs. Neurology 2009, 72, 7 Suppl, S65-73). Current research is focused on preventing neuronal dopaminergic degeneration and on the discovery of new drugs, levodopa alternatives, to manage to stop the progress of the disease and even to generate new dopaminergic type neurons. Recently different chemical families have emerged with potential in this pathology, phosphodiesterase inhibitors being one of them (Use of pde7 inhibitors for the treatment of movement disorders, USPTO Application: 20080260643, WO2008/113881). Given our prior experience in this area (Castaño, T.; Wang, H.; Campillo, N. E.; Ballester, S.; González-Garcia, C.; Hernández, J.; Pérez, C.; Cuenca, J.; Pérez-Castillo, A.; Martinez, A.; Huertas, O.; Gelpi, J. L.; Luque, F. J.; Ke, H.; Gil, C., Synthesis, structural analysis, and biological evaluation of thioxoquinazoline derivatives as phosphodiesterase 7 inhibitors. ChemMedChem. 2009, 4, 866-876), we demonstrate the use of heterocyclic quinazoline derivatives as effective agents in Parkinson models in vivo and propose their use not only in this neurodegenerative pathology but also in other neurological diseases due to their neuroprotective effect in all pathologies of the nervous system occurring with neuronal death.

BRIEF DESCRIPTION OF THE INVENTION

An object of the present invention is the use of a compound of formula (I):

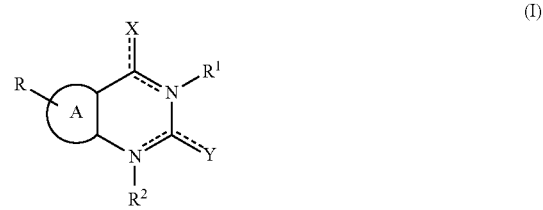

(I)

wherein:
A, is fused carbocycle or heterocycle optionally substituted with 5, 6 or 7 members saturated or unsaturated,
- - - may be a double bond;
X and Y, are selected independently from the group consisting of hydrogen, alkyl, =O, =S, aryl, O-alkyl, O-aryl, S-alkyl or —S-aryl; and
R, $R^1$, $R^2$ and $R^3$ selected independently from the group consisting of hydrogen, halogen, alkyl, haloalkyl, aryl, cycloalkyl, $(CH_2)_n$-aryl, heteroaryl, —$OR^3$; —$C(O)OR^3$, $(CH_2)_n$—$C(O)OR^3$ or —$S(O)_t$—, wherein n is greater than or equal to 0 and wherein t is 1 or 2,
or a pharmaceutically acceptable salt, derivative, prodrug, solvate or stereoisomer thereof, to produce a medicament for the treatment and/or prevention of neurodegenerative diseases, including, but not limited to, Parkinson's disease Alzheimer's disease, amyotrophic lateral sclerosis, brain ischemia, and/or of pathologies or neurological diseases wherein the dopaminergic system is involved, including, but not limited to, post-encephalitic parkinsonism, dystonias, Tourette's syndrome, periodic limb movement disorders, restless legs syndrome, attention deficit disorders with hyperactivity.

DETAILED DESCRIPTION OF THE INVENTION

The present invention is based on the fact that the inventors have demonstrated that the compounds of formula (I) are neuroprotective in primary cultures of astrocytes and glia and/or dopaminergic cell lines (Examples 1-2), as well as in an in vivo model of lipopolysaccharide (LPS)-induced neurotoxicity (Example 3). In addition, the inventors have demonstrated that the compounds are capable of crossing the blood-brain barrier in vitro and have antioxidant properties, meaning that they can be used in the production of pharmaceutical compositions for the treatment and/or prevention of neurodegenerative diseases and/or neurological diseases.

Therefore, one object of the present invention is the use of a compound of formula (I):

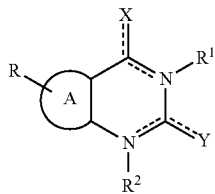

(I)

wherein:
A, is a fused carbocycle or heterocycle optionally substituted with 5, 6 or 7 members saturated or unsaturated,
- - - may be a double bond;
X and Y, are independently selected from the group consisting of hydrogen, alkyl, =O, =S, aryl, O-alkyl, O-aryl, S-alkyl or —S-aryl; and
R, $R^1$, $R^2$ and $R^3$ are independently selected from the group consisting of hydrogen, halogen, alkyl, haloalkyl, aryl, cycloalkyl, $(CH_2)_n$-aryl, heteroaryl, —$OR^3$; —$C(O)OR^3$, $(CH_2)_n$—$C(O)OR^3$ or —$S(O)_t$—, wherein n is greater than or equal to 0 and wherein t is 1 or 2,
or a pharmaceutically acceptable salt, derivative, prodrug, solvate or stereoisomer thereof,
to produce a medicament for the treatment and/or prevention of neurodegenerative and/or neurological diseases.

Preferably, A is a carbocycle with 6 members. More preferably, A is phenyl.

In a preferred embodiment, the invention relates to the use of a compound of formula (II):

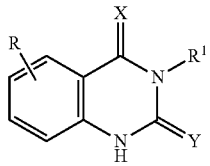

(II)

wherein
X and Y are independently selected from O or S; and
R and $R^1$ are independently selected from the group consisting of hydrogen, halogen, alkyl, haloalkyl, aryl, cycloalkyl, $(CH_2)_n$-aryl, heteroaryl, —$OR^3$; —$C(O)OR^3$, $(CH_2)_n$—$C(O)OR^3$ or —$S(O)_t$—, wherein $R^3$ is selected between hydrogen, alkyl, aryl or cycloalkyl, n is greater than or equal to 0 and t is 1 or 2,
or a pharmaceutically acceptable salt, derivative, prodrug, solvate or stereoisomer thereof,
to produce a medicament for the treatment and/or prevention of neurodegenerative and/or neurological diseases.

Preferably, X is O and Y is S.
Preferably, X is S and Y is S.
Preferably, R is selected between H or $C_1$-$C_6$ alkyl. More preferably, R is methyl.

In another preferred embodiment, the invention relates to the use of a compound of formula (III):

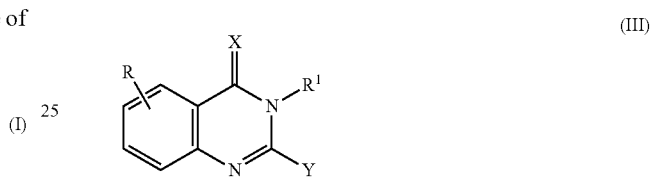

(III)

wherein:
X is selected between O or S and Y is selected between O-aryl or S-alkyl; and
R and $R^1$ are independently selected from the group consisting of hydrogen, halogen, alkyl, haloalkyl, aryl, cycloalkyl, $(CH_2)_n$-aryl, heteroaryl, —$OR^3$; —$C(O)OR^3$, $(CH_2)_n$—$C(O)OR^3$ or —$S(O)_t$—, wherein $R^3$ is selected between hydrogen, alkyl, aryl or cycloalkyl, n is greater than or equal to 0 and t is 1 or 2
or a pharmaceutically acceptable salt, derivative, prodrug, solvate or stereoisomer thereof,
to produce a medicament for the treatment and/or prevention of neurodegenerative and/or neurological diseases.

Preferably, X is O.
Preferably, X is S.
Preferably, Y is S-alkyl $C_1$-$C_6$. More preferably, Y is S—$CH_3$.
Preferably, R is selected between H or $C_1$-$C_6$ alkyl. More preferably, R is methyl.
Preferably, $R_1$ is phenyl substituted or non-substituted. More preferably, $R_1$ is phenyl substituted by at least one halogen selected between Br or F.

A particular object of the invention consists of the use of a compound of the invention of formula (I) selected from the following group:
3-Phenyl-4-oxo-2-thioxo-1,2,3,4-tetrahydroquinazoline,
3-(2,6-Difluorophenyl)-4-oxo-2-thioxo-1,2,3,4-tetrahydroquinazoline,
3-(2-Bromophenyl)-8-methyl-4-oxo-2-thioxo-1,2,3,4-tetrahydroquinazoline
3-(2,6-Difluorophenyl)-8-methyl-2-methylthio-4-oxo-3,4-dihydroquinazoline,
3-(2-Bromophenyl)-8-methyl-2-methylthio-4-oxo-3,4-dihydroquinazoline,
3-Phenyl-2,4-dithioxo-1,2,3,4-tetrahydroquinazoline,
3-Phenyl-2-methylthio-4-thioxo-3,4-dihydroquinazoline,
3-(2,6-Difluorophenyl)-2,4-dithioxo-1,2,3,4-tetrahydroquinazoline.

or a pharmaceutically acceptable salt, derivative, prodrug, solvate or stereoisomer thereof,
to produce a medicament for the treatment and/or prevention of neurodegenerative and/or neurological diseases.

In a preferred embodiment, the neurodegenerative and/or neurological disease is selected between Parkinson's disease, Alzheimer's disease, amyotrophic lateral sclerosis, brain ischemia, post-encephalitic parkinsonism, dystonias, Tourette's syndrome, periodic limb movement disorders, restless legs syndrome, attention deficit disorders with hyperactivity.

"Carbocycle" refers to a cyclic system consisting of just carbon and hydrogen atoms. For the purpose of this invention, the carbocycle may be a monocyclic, bicyclic or tricyclic system and may include fused systems and the cycle may be partially saturated or aromatic. Examples of these carbocycles include, but are not limited to, cycloalkyls, as defined herein, phenyl, naphthyl, anthracenyl, indanyl and similar.

"Heterocycle" refers in the present invention to a stable radical having a ring of 3 to 15 members comprising carbon atoms and one to five heteroatoms selected from the group consisting of nitrogen, oxygen and sulphur, preferably a 4 to 8-member ring with one or more heteroatoms, more preferably a 5 or 6-member ring with one or more heteroatoms. For the purpose of this invention, the heterocycle may be a monocyclic, bicyclic or tricyclic ring system, which can include condensed ring systems, and the nitrogen, carbon or sulphur atom in the heterocyclic radical can be optionally oxidised, the nitrogen atom can be optionally quaternised, and the heterocyclic radical may be partially or totally saturated or be aromatic. Examples of such heterocycles include, but are not limited to azepines, benzimidazole, benzothiazole, furane, isothiazole, imidazole, indole, piperidine, piperazine, purine, quinoline, thiadiazole, tetrahydrofurane, cumane, morpholine, pyrrole, pyrazole, oxazole, isoxazole, triazole, imidazole, etc.

The term "alkyl" refers in the present invention to radicals of hydrocarbonated chains, linear or branched, having 1 to 10 carbon atoms, preferably 1 to 6, and that bind to the rest of the molecule through a simple bond, for example, methyl, ethyl, n-propyl, i-propyl, n-butyl, terc-butyl, sec-butyl, n-pentyl, n-hexyl etc. The alkyl groups can be optionally substituted by one or more substitutes such as halogen (known as haloalkyl), hydroxyl, alkoxyl, carboxyl, carbonyl, cyan, acyl, alkoxycarbonyl, amino, nitro, mercapto and alkylthio.

"Cycloalkyl" refers in the present invention to a stable monocyclic or bicyclic radical of 3 to 10 members, preferably of 3 to 8 members and more preferably of 6 members, which is saturated or partially saturated, and which only consists of carbon and hydrogen atoms, such as cyclopentyl, cyclohexyl or adamantyl y which can be optionally substituted with one or more groups such as alkyl, halogen, hydroxyl, alkoxyl, carboxyl, cyan, carbonyl, acyl, alkoxycarbonyl, amino, nitro, mercapto and alkylthio.

The term "aryl" refers in the present invention to a radical phenyl, naphthyl, indenyl, phenantryl, or anthracyl. The radical aryl may be optionally substituted by one or more substitutes such as alkyl, haloalkyl, aminoalkyl, dialkylamino, hydroxyl, alkoxyl, phenyl, mercapto, halogen, nitro, cyan and alkoxycarbonyl.

"Heteroaryl" refers to an aryl having at least one heterocycle.

"Halogen" refers to fluorine, chlorine, bromine or iodine.

The compounds of the present invention represented by the formula (I), and more specifically, the specific compounds belonging to this previously described general formula may include isomers, depending on the presence of multiple bonds (for example, Z, E), including optic isomers or enantiomers, depending on the presence of chiral centres. The individual isomers, enantiomers or diastereoisomers and the mixtures thereof fall within the scope of the present invention. The individual enantiomers or diastereoisomers, as well as their mixtures, can be separated by conventional techniques.

As used herein, the term "derivative" includes both pharmaceutically acceptable compounds, in other words, derivatives of the compound of formula (I) which can be used to produce a medicament, as well as pharmaceutically unacceptable derivatives, since these may be useful in the preparation of pharmaceutically acceptable derivatives. The nature of the pharmaceutically acceptable derivative is not critical on condition that it is pharmaceutically acceptable.

Also, the scope of this invention includes the prodrugs of the compounds of formula (I). The term "prodrug" as used herein includes any compound derived from a compound of formula (I), for example, esters, including esters of carboxylic acids, amino acid esters, phosphate esters, metal salt sulfonate esters, etc., carbamates, amides, etc., which, when administered to an individual is capable of providing, directly or indirectly, said compound of formula (I) in said individual. Advantageously, said derivative is a compound that increases the bioavailability of the compound of formula (I) when administered to an individual or that potentiates the release of the compound of formula (I) in a biological compartment. The nature of said derivative is not critical on condition that it can be administered to an individual and provides the compound of formula (I) in a biological compartment of an individual. The aforesaid prodrug can be produced following conventional methods known to experts in the art.

The compounds of the invention may be in crystalline form as free compounds or in solvate form, intending both forms to be within the scope of the present invention. In this sense, the term "solvate", as used herein, includes both pharmaceutically acceptable solvates, in other words, solvates of the compound of formula (I) which can be used to produce a medicament, as well as pharmaceutically unacceptable solvates, which can be useful to produce pharmaceutically acceptable solvates or salts. The nature of the pharmaceutically acceptable solvate is not critical on condition that it is pharmaceutically acceptable. In a particular embodiment, the solvate is a hydrate. The solvates can be obtained by conventional solvation methods known to technicians in the art.

For therapeutic application, the compounds of formula (I), their isomers, salts, prodrugs or solvates, will come preferably in a pharmaceutically acceptable or substantially pure form, in other words, having a pharmaceutically acceptable level of purity excluding standard drugs such as diluents and carriers, and not including material considered toxic at standard dose levels.

The purity levels for the active principle are preferably higher than 50%, more preferably higher than 70%, more preferably higher than 90%. In a preferred embodiment, they are higher than 95% of the compound of formula (I), or the salts, solvates or prodrugs thereof.

Unless otherwise specified, the compounds of the invention also include compounds that differ only in the presence of one or more isotopically-enriched atoms. For example, compounds having said structure, excluding the substitution of hydrogen with a deuterium or a tritium, or the substitution of a carbon by a carbon enriched with $^{13}C$ or $^{14}C$ or nitrogen enriched with $^{15}N$, are within the scope of the invention.

The compounds of formula (I) for therapeutic use are prepared in solid form or aqueous suspension, in a pharmaceutically acceptable diluent. These preparations may be administered via any appropriate route of administration, wherefore said preparation will be formulated in the suitable pharmaceutical form for the selected route of administration. In a particular embodiment, the compound of formula (I) provided by this invention is administered orally, topically, rectally or parenterally (including subcutaneously, intraperitoneally, intradermally, intramuscularly, intravenously, etc.). A review of the different pharmaceutical forms for administering medicaments and the excipients required to obtain them can be found, for example, in the "Treaty of Galenic Pharmacy", C. Fauli i Trillo, 1993, Luzán 5, S. A. Ediciones, Madrid, or in other standard or similar Pharmacopoeias of Spain and the US.

The compounds described in the present invention, their pharmaceutically acceptable salts, prodrugs and/or solvates as well as the pharmaceutical compositions containing them can be used in conjunction with other additional drugs in order to provide a combination therapy. Said additional drugs may form part of the same pharmaceutical composition or, alternatively, may be provided in the form of a separate composition for administration simultaneously or not with the administration of the pharmaceutical composition comprising a compound of formula (I), or pharmaceutically acceptable prodrug, solvate, derivative or salt thereof.

Another additional object of the present invention consists of a method for treating a neurodegenerative and/or neurological disease comprising the administration of a therapeutically effective amount of a compound of formula (I):

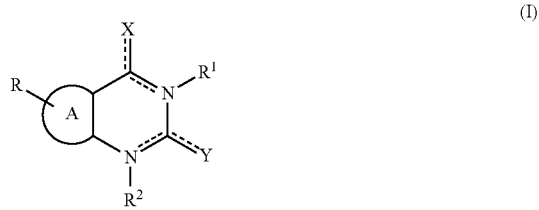

(I)

wherein:
A, is a fused carbocycle or heterocycle optionally substituted with 5, 6 or 7 members saturated or unsaturated,
- - - may be a double bond;
X and Y, are independently selected between the group consisting of hydrogen, alkyl, =O, =S, aryl, O-alkyl, O-aryl, S-alkyl or —S-aryl; and R, $R^1$, $R^2$ and $R^3$ are independently selected between the group consisting of hydrogen, halogen, alkyl, haloalkyl, aryl, cycloalkyl, $(CH_2)_n$-aryl, heteroaryl, —$OR^3$; —$C(O)OR^3$, $(CH_2)_n$—$C(O)OR^3$ or —$S(O)_t$—, wherein n is greater than or equal to 0 and wherein t is 1 or 2,
or a pharmaceutically acceptable salt, derivative, prodrug, solvate or stereoisomer thereof.

In the sense used in this description, the expression "therapeutically effective amount" refers to the quantity of agent or compound capable of having a neuroprotective effect on primary cultures of astrocytes and glia and/or on dopaminergic cell lines, calculated to produce the required effect in vivo and, in general, will be determined, among other aspects, by the inherent properties of the compounds, including the age, state of the patient, severity of the alteration or disorder, and route and frequency of administration.

Preferably the neurodegenerative and/or neurological diseases to be treated in said method are selected between Parkinson's disease, Alzheimer's disease, amyotrophic lateral sclerosis, brain ischemia, post-encephalitic parkinsonisms, dystonias, Tourette's syndrome, periodic limb movement disorders, restless legs syndrome, attention deficit disorders with hyperactivity.

The compound of the invention is compatible for use in protocols wherein the compounds of formula (I) or their mixtures are used alone or in combination with other treatments or medical procedures.

EXAMPLES OF THE INVENTION

In the following examples, the following compounds have been tested having a formula comprised within formula (I):
  3-phenyl-4-oxo-2-thioxo-1,2,3,4-tetrahydroquinazoline (Comp. 1),
  3-(2,6-difluorophenyl)-4-oxo-2-thioxo-1,2,3,4-tetrahydroquinazoline (Comp. 2),
  3-(2-bromophenyl)-8-methyl-4-oxo-2-thioxo-1,2,3,4-tetrahydroquinazoline (Comp. 3),
  3-(2,6-difluorophenyl)-8-methyl-2-methylthio-4-oxo-3,4-dihydroquinazoline (Comp. 4),
  3-(2-bromophenyl)-8-methyl-2-methylthio-4-oxo-3,4-dihydroquinazoline (Comp. 5),
  3-phenyl-2,4-dithioxo-1,2,3,4-tetrahydroquinazoline (Comp. 6),
  3-phenyl-2-methylthio-4-thioxo-3,4-dihydroquinazoline (Comp. 7),
  3-(2,6-difluorophenyl)-2,4-dithioxo-1,2,3,4-tetrahydroquinazoline (Comp 8).

Example 1

Measurement of the Neuroprotective Effect of the Compounds of Formula (I) According to Nitrite Production by the Different Cell Lines Essentially, primary cultures of microglia and astrocytes were used
(Luna-Medina, R.; Cortes-Canteli, M.; Alonso, M.; Santos, A.; Martinez, A.; Perez-Castillo, A., *Regulation of inflammatory response in neural cells in vitro by thiadiazolidinones derivatives through peroxisome proliferator-activated receptor gamma activation.* J. Biol. Chem. 2005, 280, 21453-21462). The primary cultures of astrocytes and microglia were obtained from the cortex and hippocampus of postnatal 2-day-old mice. After dissecting the cortex and hippocampus and clearing them of the meninges, cells are disintegrated by mechanical grinding and incubated with 0.25% trypsin/EDTA at 37° C. during 45 minutes. DMEM with 10% foetal serum is added to stop the digestion with trypsin and mechanical grinding of the tissue is completed. Centrifugation is applied at 800xg/5 min and the precipitate washed 3 times in EBSS; finally, cells are resuspended in DMEM plus 10% foetal serum and seeded at a density of $0.5 \times 10^5$ cells/$cm^2$. Cells are incubated for 10-12 days after which a monolayer of astrocytes is observed to which microglia cells lightly adhere. To isolate microglia cells culture bottles are incubated in a rotary agitator at 37° C. during 4 hours at 250 rpm and the medium containing microglia centrifuged at 1500xg/5 min. Microglia cells are resuspended in DMEM/10% FBS and seeded at a density of $2\text{-}4 \times 10^5$ cells/cm$^2$. After 1 hour of incubation, to allow them to adhere to the plate, they are washed with TD and incubated in DMEM/10% FBS during 24 hours, after which cells are used in the various experiments. The level of purity of these cultures is determined by immunocytochemistry assays with neuron-specific antibodies (β-tubulin and MAP2), astrocytes (GFAP), oligodendrocytes (CNPase) and microglia (Ox42).

Figure 1:
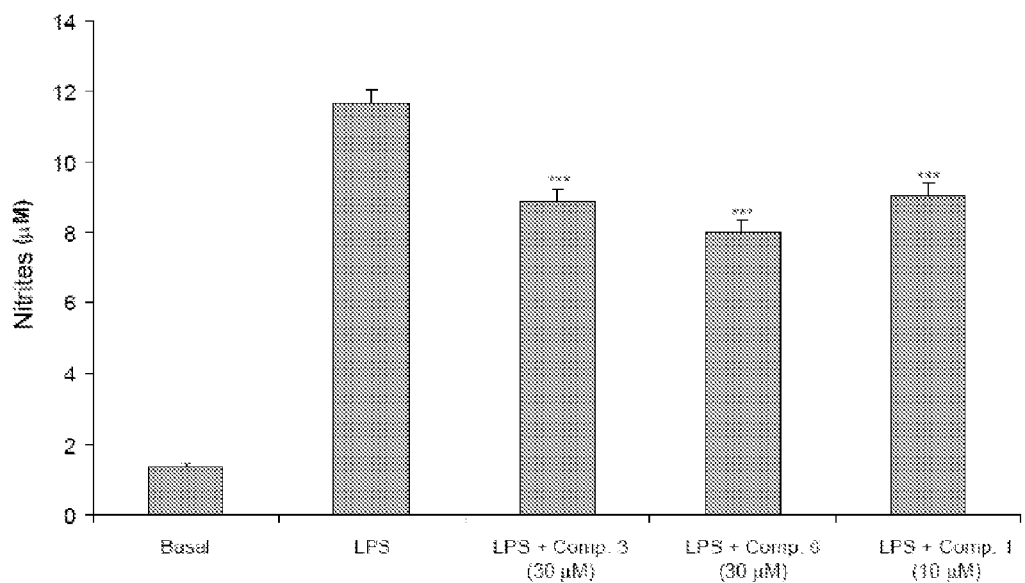
FIG. 1.—Neuroprotective effect of the compounds on lipopolysaccharide (LPS)-stimulated primary astrocyte cultures.
Figure 1:
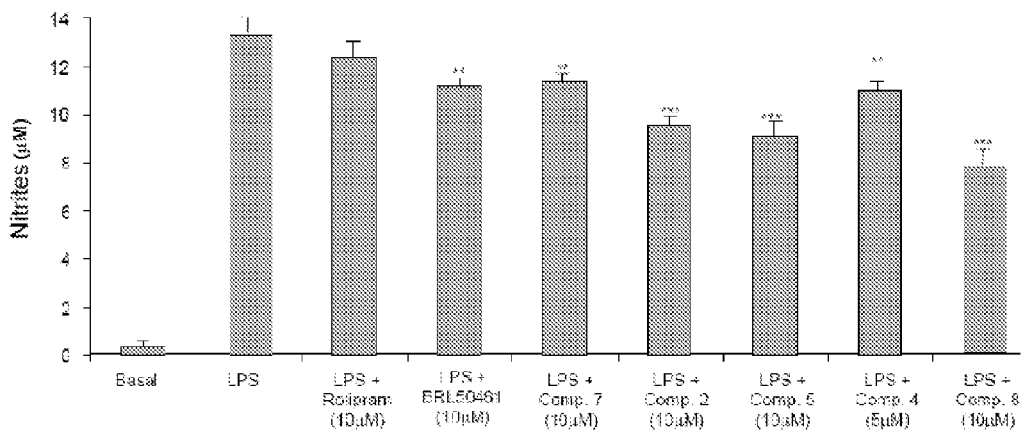
Figure 1:
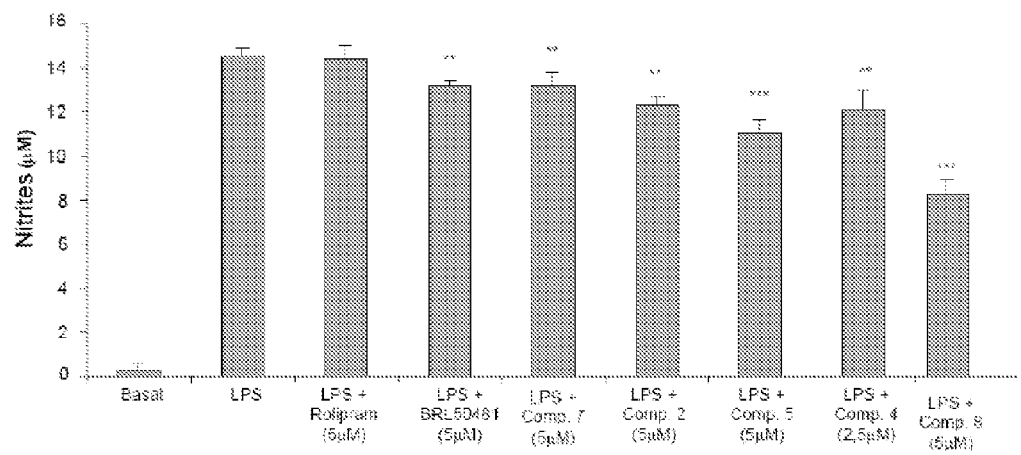
Figure 2:
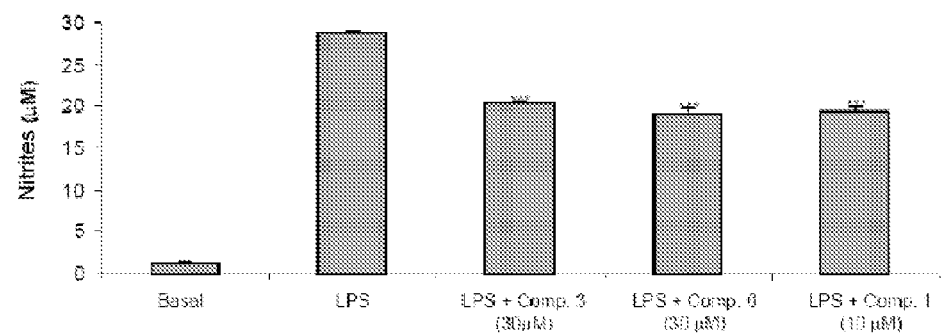
FIG. 2.—Neuroprotective effect of the compounds on LPS-stimulated primary microglia cultures.
Figure 2:
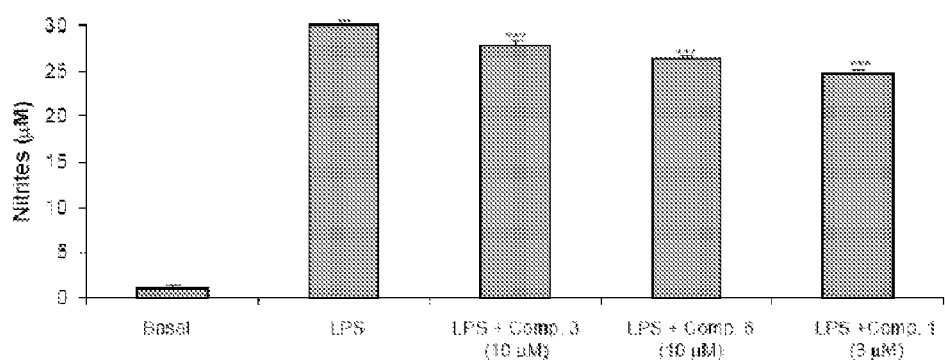
Figure 2:
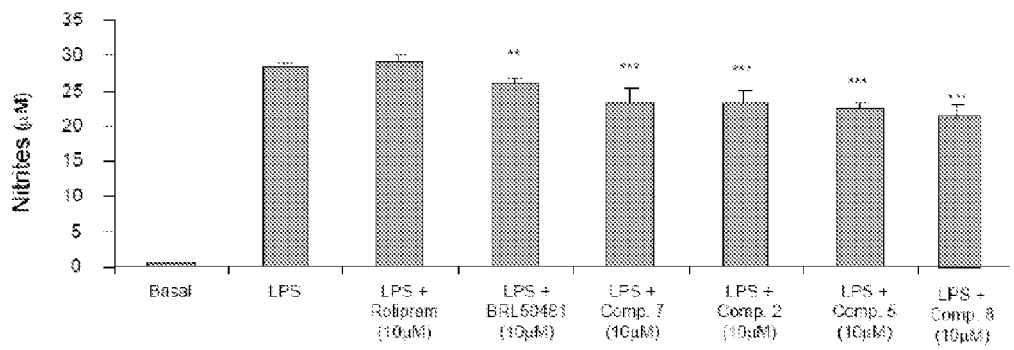
Figure 2:
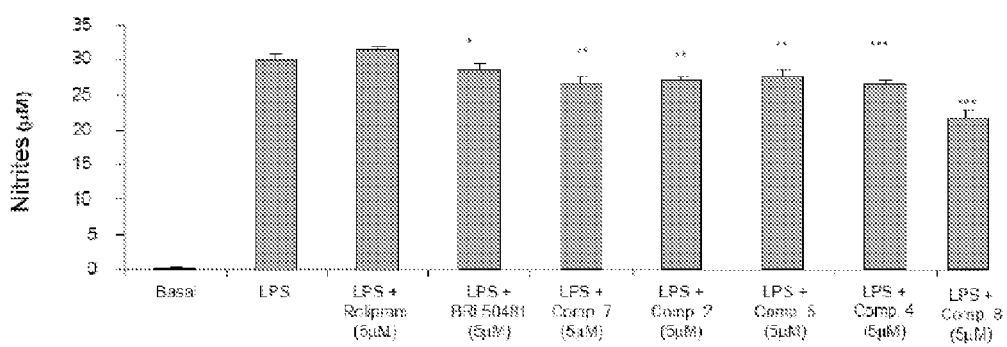

Cell cultures of astrocytes and microglia are treated with LPS (10 μg/ml) in the absence and presence of the different compounds. The compounds are added 1 hour before the inflammatory stimulus. At different times after incubation, cells are washed and gathered for corresponding measurement of the effect of the compounds on NO (nitric oxide) production by iNOS (inducible nitric oxide synthase) as an indicator of neural damage due to inflammatory processes (Kroncke K. D.; Fehsel K.; Kolb-Bachofen V., Nitric oxide: cytotoxicity versus cytoprotection—how, why, when, and where? Nitric Oxide 1997, 1, 107-120). To this effect, after 24 hours of incubation the quantity of nitrites, one of the oxidation products of NO, is determined. To achieve this, the method based on the Griess reaction is used (Griess, P. Bemerkungen zu der abhandlung der H. H. Weselsky and Benedikt Ueber einige azoverbindungen. Chem. Ber. 1879, 12, 426-428): 100 μl of supernatant from the cultures is mixed with 100 μl of Griess reagent in a 96-well plate and incubated during 15 min at room temperature. Next, absorbance is measured at 540 nm in a microplate reader. The amount of nitrites produced is determined using a standard sodium nitrite curve. Reference compounds in the assay: Rolipram and BRL50481.
See FIGS. 1 and 2

Example 2

Neuroprotection Assay of SH-SY5Y Neuroblastoma Cells

Figure 3:
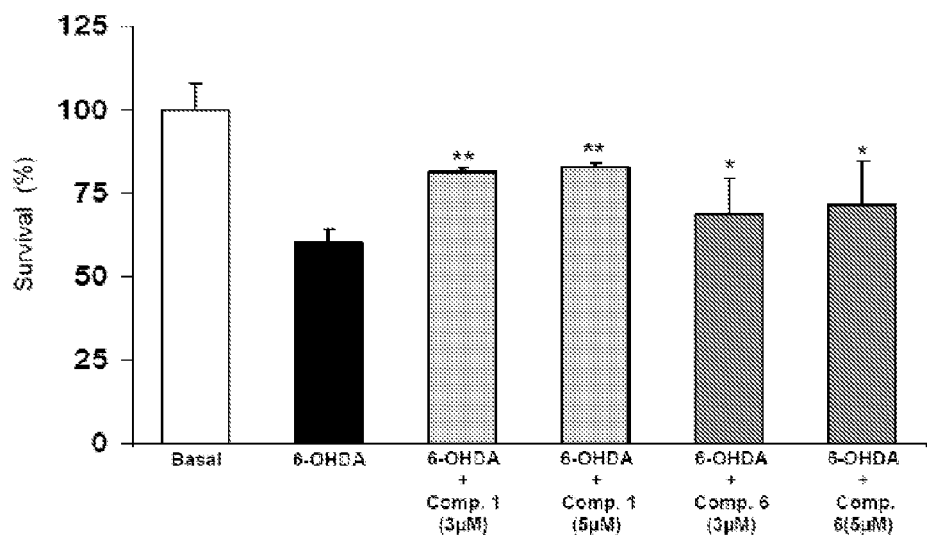
FIG. 3.—Neuroprotection of the SH-SY5Y dopaminergic cell line
FIG. 4.—(A) Viability of the dopaminergic cells of "substantia nigra" neurons following LPS-induced damage. (B) Microglial activation in response to LPS.

The human neuroblastoma cell line SH-SY5Y is exposed to a 50 μM concentration of neurotoxin 6-hydroxydopamine (6-OHDA) in the presence or absence of S14 or TC3.6. 6-OHDA is a highly toxic substance for these cells and incubation with it provokes significant cell death, it being commonly used as an in vitro cell model of parkinsonism (Mendez, J. S.; Finn, B. W., Use of 6-hydroxydopamine to create lesions in catecholamine neurons in rats. J Neurosurg. 1975, 42, 166-173.). Cellular viability is determined using the bromide compound of 3(4,5-dimethylthiazol-2)-2,5-diphenyltetrazolium (MTT) which measures the integrity of the mitochondrial function. Each data represents the average ±SD of five replicates in three different experiments. *$P<0.05$ and **$P<0.01$, statistically significant differences between the different experiments. See FIG. 3.

Example 3

Neuronal Survival in Vivo

Figure 4:
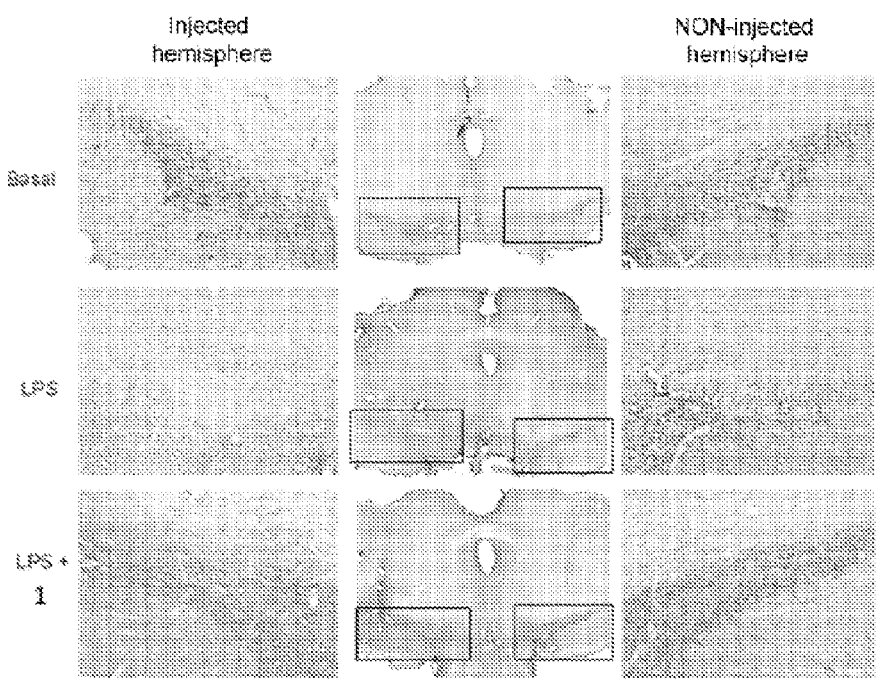
Figure 4:
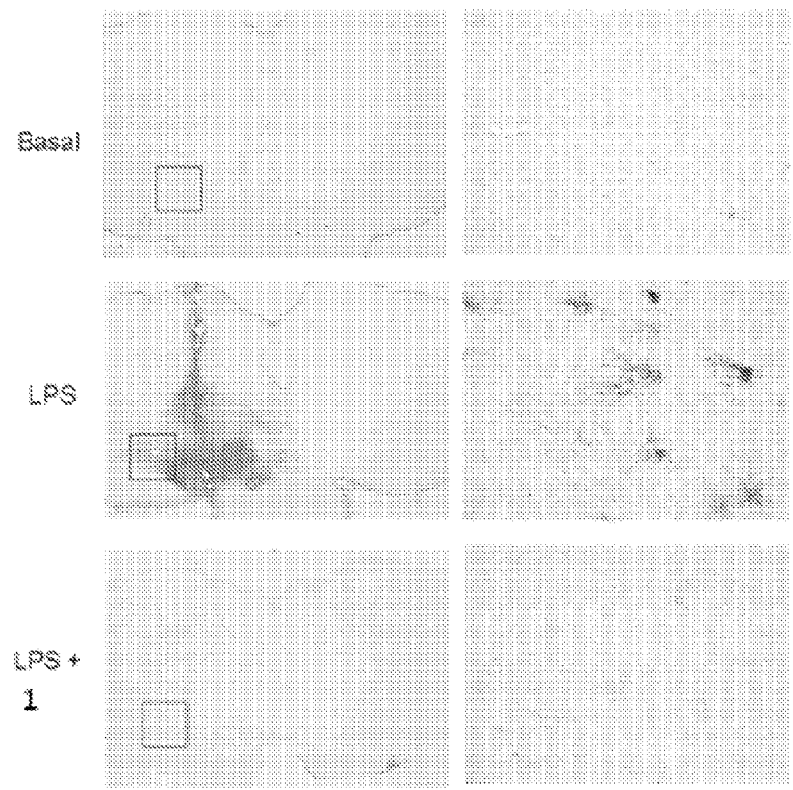

The lipopolysaccharide LPS, 5 μg) or vehicle is injected unilaterally into the substantia nigra (SN) of adult rats. One of the animal groups additionally receives 5 nmol of S14 in the injection. Three days after the operation, the animals are given an intracardial perfusion of 4% paraformaldehyde in PBS, during approximately 45-60 minutes. Following perfusion the brain is extracted and left in the paraformaldehyde solution during 24 hours after which it is changed to a solution of 4% paraformaldehyde/30% sucrose for approximately 48 hours. Brains fixed in this way are frozen in carbonic snow taking cuts of 25 mm in a cryostat. For single-antibody staining, the ABC system is used (ABC Elite kit, Vector). Selected cuts are washed in PBS and treated with a methanol/PBS/$H_2O/H_2O_2$ solution in order to block endogenous peroxidases. After washing with PBS cuts are blocked with 0.1 M lysine/5% serum/0.1% triton X-100/4% BSA in PBS. Incubation with the corresponding primary antibody is carried out at 4° C. during 18 hours in PBS with 4% BSA, 1% serum and 0.1% triton X-100. After washing with PBS, cuts are incubated during 1 hour at room temperature with the corresponding biotynilated secondary antibody in PBS containing 4% BSA, 1% serum and 0.1% triton X-100, at a 1:200 dilution. After incubation the ABC kit is added and cuts are incubated during 1 hour. After washing with PBS they are revealed with DAB and mounted onto gelatine-coated slides and dehydrated for subsequent microscopic observation. Neuronal integrity is measured through conventional Nissl staining and the survival of dopaminergic cells by staining the cuts with an anti-tyrosine hydroxylase (TH) specific antibody. Glial activation is determined using anti-GFAP antibodies (stains reactive astrocytes) and anti-CD11 b (OX-42, stains activated microglia).
See FIG. 4

Example 4

Measurement of the Antioxidant Effect of the Compounds of Formula (I)

Given that in many neurodegenerative diseases neuronal death occurs due to oxidative stress, the capacity of these compounds to capture free radicals has been evaluated using the ORAC methodology.

Determination is following the ORAC-FL method of Ou et al. partially adapted by BMG LABTECH (BMG LABTECH Application note 148 (2006): ORAC Assay on the FLUOstar OPTIMA to Determine Antioxidant Capacity. http://www.b-mglabtech.com/application-notes/fluorescence-intensity/orac 148.cfm). The FLUOstar Optima (BMG Labtechnologies GmbH, Offenburg, Germany) plate reader was used with an excitation filter at 485 nm excitation and 520 nm emission. 2,2'-Azobis-(amidinopropane) dihydrochloride (AAPH), (±)-6-hydroxy-2,5,7,8-tetramethylchromane-2-carboxylic acid (trolox) and fluorescein (FL) are purchased from Sigma-Aldrich. The reaction is carried out in 75 mM phosphate buffer (pH 7.4) and a final reaction volume of 200 μL. The antioxidant (25 μL) and fluorescein (150 μL; 10 nM) are placed on black 96-well plates (96F untreat, Nunc™). The mixture is pre-incubated during 30 minutes at 37° C. afterwards rapidly adding a solution of AAPH (25 μL, 240 mM), using a multi-channel pipette. The microplate is rapidly placed on the reader and fluorescence is measured every 90 sec during 90 min. The 96-well plate is agitated automatically before each reading. The compounds are tested at 4 different concentrations (10-1 μ). A blank is also placed (FL+AAPH in phosphate buffer) and as reference compound four concentrations of trolox (10-1 μM). All reactions are carried out in duplicate, and at least three different tests per compound.

Data are exported to an Excel spreadsheet (Microsoft), representing absorbance versus time and subsequently the area under curve is calculated following the formula (1)

$$AUC = f_1/f_0 + f_2/f_0 + \ldots + f_{34}/f_0 + (f_{35}/f_0)$$

wherein: AUC=area under curve
$f_0$=fluorescence measured at time 0
$f_t$=fluorescence measured at time t The net AUC values of each compound are determined by subtracting from the AUC value of the compound the AUC value of the blank (FL+AAPH in phosphate buffer).

The measurement of antioxidant is expressed in trolox equivalents. Relative trolox equivalents are calculated according to formula (2):

$$\left( \frac{AUCsample - AUCblank}{AUCTrolox - AUCblank} * \frac{[Trolox]}{[sample]} \right) \quad (2)$$

The results are shown in table 1.

TABLE 1

Antioxidant capacity of the compounds in trolox equivalents

| Compound | Trolox equivalents |
|---|---|
| 1 | 1.19 |
| 2 | Not to 10 μM |
| 3 | 1.31 |
| 4 | 0.13 |
| 5 | Not to 10 μM |
| 6 | 0.46 |
| 7 | 0.37 |
| 8 | n.d. | n.d. = not determined

Example 5

Measurement of the Blood Brain Permeability of the Compounds of Formula (I)

The passing of the blood brain barrier is determined in vitro by means of a permeability assay using an artificial membrane, PAMPA (Parallel Artificial Membrane Permeation Assay), following the procedure previously optimised in the authors' laboratories. Two 96-well plates (Millipore) are used on a sandwich type assembly. The donating microplate contains a PVDF filter at the bottom of each well where a lipid extract of pig is placed, acting as the biological barrier. Each assay is validated with 8 commercial drugs whose CNS penetration is known.

Initially, wavelengths are determined of the absorption spectrum of a solution of each compound (1 mg in 5 ml of PBS/EtOH 70:30), whose absorbance levels must be between 1-0.8 so as to, subsequently, measure permeability.

Once the required wavelengths have been selected, 180 μL of each solution (1 mg of compound in 5 mL of PBS/EtOH 70:30) is added to each well of the donor plate. The artificial membrane is coated with 4 μL of PBL solution in 20 mg/ml dodecane. 180 μl of the buffer solution (pH=7.4) is added to the acceptor plate, next forming a "sandwich"-type system in such a way that the donor plate is above the acceptor plate through the artificial membrane. This system is incubated for 4 h without agitation at room temperature. The absorbance levels of the acceptor plate are measured using a UV spectrophotometer on a 96-well plate with 130 μl in each one. The results are expressed as the average value of three independent tests each one containing three repetitions of each derivative to be analysed. The differences between final and initial absorbance levels are correlated with permeability.

The method employed was validated in the same conditions using 9 commercial products whose capacity to penetrate the CNS is known. In this way, a good linear relationship was obtained between the experimental and described permeability. Based on this correlation it was possible to establish limits to predict the passing of the blood brain barrier. Therefore it is considered that a molecule passes the blood brain barrier (CNS+) when its permeability (Pe) is above $4 \cdot 10^{-6} \cdot cm \cdot s^{-1}$ and therefore, it would be capable of reaching its therapeutic target situated in the CNS. At the same time, a molecule is considered not to pass the blood brain barrier (CNS−) when Pe is below $2 \cdot 10^{-6} \cdot cm \cdot s^{-1}$. Intermediate values present uncertainty (CNS+/−).

The data is shown in table 2. Most of the compounds evaluated are capable of passing the blood brain barrier according to this methodology.

TABLE 2

Passage of the blood brain barrier of the compounds

| Compound | CNS Penetration | Bibliography |
|---|---|---|
| Chlorpromazine | + | 6.5 |
| Desipramine | + | 12 |
| Enoxacine | − | 1.8 |
| Hydrocortisone | − | 1.9 |
| Imipramine | + | 13 |
| Ofloxacin | − | 0.8 |
| Promazine | + | 8.1 |
| Verapamil | + | 16 |
| Atenolol | − | 0.8 |
| Comp. 1 | + | |
| Comp. 2 | + | |
| Comp. 3 | + | |
| Comp. 4 | n.d. | |
| Comp. 5 | − | |
| Comp. 6 | + | |
| Comp. 7 | n.d. | |
| Comp. 8 | + | | n.d. = not determined due to lack of solubility in the experimental medium

The invention claimed is:

1. A method for reducing neural cell damage in a patient suffering from a neurodegenerative disease or condition comprising the administration to a patient in need of such treatment a therapeutically effective amount of at least one compound of formula (I) or any pharmaceutically acceptable salt, derivative, prodrug, solvate or stereoisomer thereof, or a pharmaceutical composition thereof:

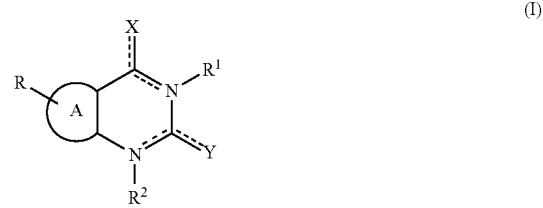

wherein:
A is phenyl,
- - - may be a double bond;
X is selected from the group consisting of hydrogen, alkyl, =O, =S, aryl, O-alkyl, O-aryl, S-alkyl and —S-aryl; Y is =S or —S-alkyl; and R, R¹, and R² are independently selected from the group consisting of hydrogen, halogen, alkyl, haloalkyl, aryl, cycloalkyl, (CH₂)ₙ-aryl, —OR³; —C(O)OR³, (CH₂)ₙ—C(O)OR³ and —S(O)ₜ—, wherein R³ is selected from hydrogen, alkyl, aryl, and cycloalkyl, n is greater than or equal to 0, and t is 1 or 2, provided that when R¹ is aryl, cycloalkyl, or (CH₂)ₙ-aryl, X is =S or Y is S-alkyl.

2. A method for reducing neural cell damage in a patient suffering from a neurodegenerative disease or condition comprising the administration to a patient in need of such treatment a therapeutically effective amount of at least one compound of formula (II) or any pharmaceutically acceptable salt, derivative, prodrug, solvate or stereoisomer thereof, or a pharmaceutical composition thereof:

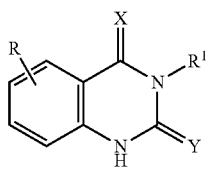

(II)

wherein X is selected from O and S; Y is =S or —S-alkyl; and R and R¹ are independently selected from the group consisting of hydrogen, halogen, alkyl, haloalkyl, aryl, cycloalkyl, (CH₂)ₙ-aryl, heteroaryl, —OR³; —C(O)OR³, (CH₂)ₙ—C(O)OR³ and —S(O)ₜ—, wherein R³ is selected from hydrogen, alkyl, aryl and cycloalkyl, n is greater than or equal to 0 and t is 1 or 2;

provided that when R¹ is aryl, cycloalkyl, or (CH₂)ₙ-aryl, X is =S or Y is S-alkyl.

3. The method according to claim 2 wherein X is O and Y is S.

4. The method according to claim 2 wherein X is S and Y is S.

5. The method according to claim 2 wherein R is selected from H or alkyl C₁-C₆.

6. The method according to claim 1 wherein R₁ is phenyl substituted or non-substituted.

7. The method according to claim 1 wherein the compound is selected from the following group:
- 3-phenyl-4-oxo-2-thioxo-1,2,3,4-tetrahydroquinazoline,
- 3-(2,6-difluorophenyl)-4-oxo-2-thioxo-1,2,3,4-tetrahydroquinazoline,
- 3-(2-Bromophenyl)-8-methyl-4-oxo-2-thioxo-1,2,3,4-tetrahydroquinazoline,
- 3-(2,6-Difluorophenyl)-8-methyl-2-methylthio-4-oxo-3,4-dihydroquinazoline,
- 3-(2-Bromophenyl)-8-methyl-2-methylthio-4-oxo-3,4-dihydroquinazoline,
- 3-Phenyl-2,4-dithioxo-1,2,3,4-tetrahydroquinazoline,
- 3-Phenyl-2-methylthio-4-thioxo-3,4-dihydroquinazoline, and
- 3-(2,6-Difluorophenyl)-2,4-dithioxo-1,2,3,4-tetrahydroquinazoline.

8. A method of reducing neural cell damage in a patient, comprising administering to the patient a therapeutically effective amount of at least one compound of formula (I) or any pharmaceutically acceptable salt, derivative, prodrug, solvate or stereoisomer thereof, or a pharmaceutical composition thereof:

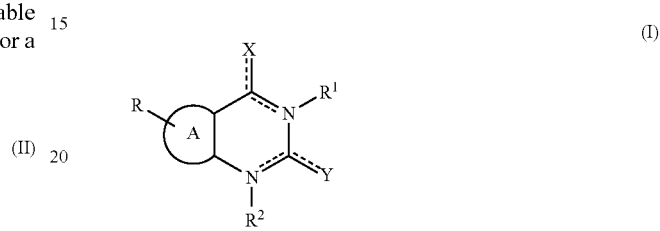

(I)

wherein:
A is phenyl,
- - - may be a double bond;
X is selected from the group consisting of hydrogen, alkyl, =O, =S, aryl, O-alkyl, O-aryl, S-alkyl and —S-aryl; Y is =S or —S-alkyl; and R, R¹, and R² are independently selected from the group consisting of hydrogen, halogen, alkyl, haloalkyl, aryl, cycloalkyl, (CH₂)ₙ-aryl, —OR³; —C(O)OR³, (CH₂)ₙ—C(O)OR³ and —S(O)ₜ—, wherein R³ is selected from hydrogen, alkyl, aryl, and cycloalkyl, n is greater than or equal to 0, and t is 1 or 2;

provided that when R¹ is aryl, cycloalkyl, or (CH₂)ₙ-aryl, X is =S or Y is S-alkyl;

to protect the neural cells from damage due to inflammatory processes.

9. The method according to claim 8 wherein the neural cell damage is associated with a neurodegenerative and/or neurological disease selected from the following group: Alzheimer's disease, Parkinson's disease, amyotrophic lateral sclerosis, brain ischemia, post-encephalitic parkinsonisms, dystonias, Tourette's syndrome, periodic limb movement disorders, restless legs syndrome, and attention deficit disorders with hyperactivity.

10. The method of claim 8, wherein the neural cell damage is associated with a neurodegenerative and/or neurological disease or condition.

11. The method of claim 8, wherein the neurodegenerative and/or neurological disease or condition is Alzheimer's disease or Parkinson's disease.

* * * * *